(12) United States Patent
Suzuki et al.

(10) Patent No.: US 7,413,304 B2
(45) Date of Patent: Aug. 19, 2008

(54) OPHTHALMIC APPARATUS

(75) Inventors: Takayoshi Suzuki, Hamamatsu (JP); Norihiko Yokoi, Street 251-1 Kamigoryo Kamiecho, Kita-ku, Kyoto-shi, Kyoto-Fu 603-8147 (JP)

(73) Assignees: Kowa Company Ltd (JP); Norihiko Yokoi (JP)

( * ) Notice: Subject to any disclaimer, the term of this patent is extended or adjusted under 35 U.S.C. 154(b) by 0 days.

(21) Appl. No.: 11/821,976

(22) Filed: Jun. 26, 2007

(65) Prior Publication Data
US 2007/0258043 A1     Nov. 8, 2007

Related U.S. Application Data

(63) Continuation of application No. 09/273,286, filed on Mar. 19, 1999, now Pat. No. 7,278,740.

(30) Foreign Application Priority Data
Mar. 20, 1998 (JP) .................................. 98/71615

(51) Int. Cl.
*A61B 3/10* (2006.01)
*A61B 3/02* (2006.01)
*A61B 5/00* (2006.01)

(52) U.S. Cl. .......................... 351/205; 351/214; 351/222
(58) Field of Classification Search ................. 351/205, 351/214, 215, 216, 222, 233; 600/366, 576; 424/78.04; 953/514, 912
See application file for complete search history.

(56) References Cited

U.S. PATENT DOCUMENTS

| | | | | |
|---|---|---|---|---|
| 4,269,197 A | * | 5/1981 | Gilbard | 600/576 |
| 4,951,683 A | * | 8/1990 | Davis | 600/383 |
| 5,352,445 A | * | 10/1994 | Lavaux | 424/78.04 |
| 5,719,659 A | * | 2/1998 | Suzuki | 351/215 |

* cited by examiner

*Primary Examiner*—Ricky L Mack
*Assistant Examiner*—Brandi N Thomas
(74) *Attorney, Agent, or Firm*—Adams & Wilks

(57) ABSTRACT

A grid formed with apertures of a predetermined shape is illuminated with light from a lamp and projected onto a tear meniscus accumulated on the lower eyelid. The aperture image projected on the tear film is imaged by a CCD camera. The tear meniscus functions as a concave mirror, so that the magnification factor depends on the radius of meniscus curvature. A processor calculates the magnitude of the grid image and evaluates the radius of meniscus curvature. Since the volume of lacrimal fluid varies depending upon the radius of meniscus curvature, the latter is used as a value representing the lacrimal fluid volume for dry eye diagnose purposes.

18 Claims, 4 Drawing Sheets

F I G. 1a
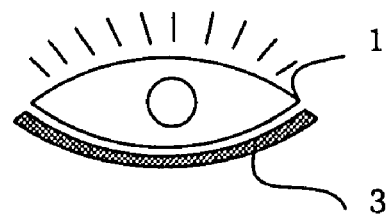
F I G. 1b
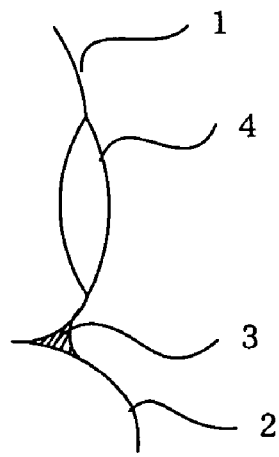
F I G. 1c            F I G. 1d
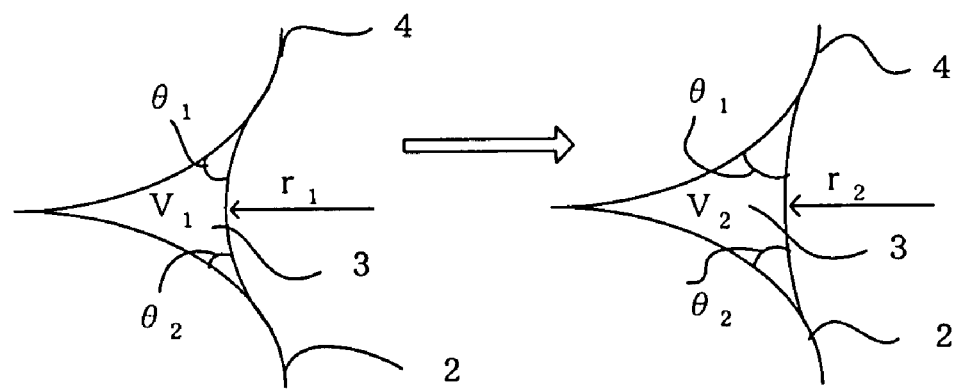

OPHTHALMIC APPARATUS

CROSS REFERENCE TO RELATED APPLICATION

The present application is a continuation of prior U.S. application Ser. No. 09/273,286, filed on Mar. 19, 1999, now U.S. Pat. No. 7,278,740 which is hereby incorporated by reference, and priority thereto for common subject matter is hereby claimed.

BACKGROUND OF THE INVENTION

1. Field of the Invention

The present invention relates to an ophthalmic apparatus, and more particularly to an ophthalmic apparatus for non-contact measurement of the physical quantity of lacrimal fluid collected on the lower eyelid.

2. Description of the Prior Art

Recent years have seen an increase in the numbers of people suffering from dry eyes caused by working with VDTs (visual display terminals) or working in rooms in which the air is dried out by air conditioning systems. Dry eyes can result in a number of ophthalmic conditions, such as damage to the corneal epithelium and conjunctiva. As such, the diagnosis of dry eye syndrome is becoming an important part of ophthalmic diagnostic procedure.

Conventional methods of diagnosing dry eye include examining vital stainings and volume of lacrimal fluid. However, such methods involve discomfort to the patient caused by the application of a solution or contacting the eye with an instrument. To detect the dry eyes in a non-contact manner, methods have been tried involving projecting a beam of coherent light onto the eye and examining interference fringes formed by the tear film layer. In the apparatus of such systems, color images of interference fringes (rainbow-colored interference patterns) formed by the tear film lipid layer of an eye to be examined are photoelectrically converted by a photoelectric element in a light-receiving system and shown on a display means. The presence of dry eye can then be readily diagnosed by examining the interference pattern indicating the condition of the tear film layer.

However, a problem with the interference fringes produced by tear film lipid layer with the conventional systems is the low contrast of the fringes, which makes it difficult to obtain a good ophthalmic diagnosis based on the fringes. Another problem is that the examiner directly observes the color patterns on the display screen to evaluate the grade of the dry eye condition, so only qualitative measurement is possible.

The object of the present invention is to provide an ophthalmic apparatus that enables diagnosis of dry eye condition by quantitatively measuring the physical quantity of lacrimal fluid collected on the border of the lower eyelid.

SUMMARY OF THE INVENTION

In accordance with the present invention, the above object is attained by an ophthalmic apparatus comprising a light control means formed with an aperture having a predetermined shape, means for projecting the aperture onto a surface of tear film collected on a lower eyelid, means for imaging the aperture projected on the tear film surface, and a means for evaluating a physical quantity of lacrimal fluid based on the image of the aperture thus obtained.

The tear film surface on the border of the lower eyelid (tear meniscus) functions like a concave mirror, so the magnification factor of the imaged aperture depends on the radius of meniscus curvature. In this invention, the magnification factor of the aperture image is obtained, giving the radius of meniscus curvature. The radius of meniscus curvature has a bearing on the volume of lacrimal fluid affecting the dry eye condition, so obtaining the radius of meniscus curvature makes it possible to evaluate quantitatively the degree of severity of the dry eye condition, or the phase into improvement thereof.

The above and other features of the present invention will become apparent from the following description made with reference to the drawings.

BRIEF EXPLANATION OF THE DRAWINGS

FIGS. 1a and 1b are diagrams illustrating the state of tear film collected in the lower eyelid, and FIGS. 1c and 1d are diagrams illustrating the relationship between the radius of meniscus curvature and the volume of lacrimal fluid;

DESCRIPTION OF THE PREFERRED EMBODIMENT

FIG. 1 illustrates the principle of a meniscometer for measuring the quantity of lacrimal fluid. A tear film from the outermost layer 1 of the eye is comprised of lipid, acqueous and mucin layers: the lipid layer is secreted from the Meibomian gland and is subjected to pressure when the eyelid closes. When this happens, a tear film 3 accumulates on the lower eyelid border, as shown in FIGS. 1a and 1b. An examination for dry eye is conducted with respect to the volume of lacrimal fluid on the border of the lower eyelid, with less lacrimal fluid indicating a more severe dye eye condition.

The relationship between tear volume V and radius of meniscus curvature r of the surface of the tear film 3 is that, since the cornea 4 and the eyelid 2 are both curved, a larger V results in a larger r. This relationship is illustrated by FIGS. 1c and 1d. If lacrimal fluid volume V increases from V1 to V2, the radius of meniscus curvature also increases from r1 to r2. Here, $\theta1$, $\theta2$ are constants determined by the surface tension. While these constants vary according to the severity of the dry eye condition, compared to the change in r, such change is negligibly small.

In the present invention, the volume V of lacrimal fluid is determined by measuring the radius of meniscus curvature r (tear meniscus). For this, in accordance with the invention, a grid image is projected onto the tear film surface, and the physical quantity of the lacrimal fluid, that is, the radius of meniscus curvature r, is measured by analyzing the grid image. FIG. 2 shows the configuration of this principle.

Figure 2A:
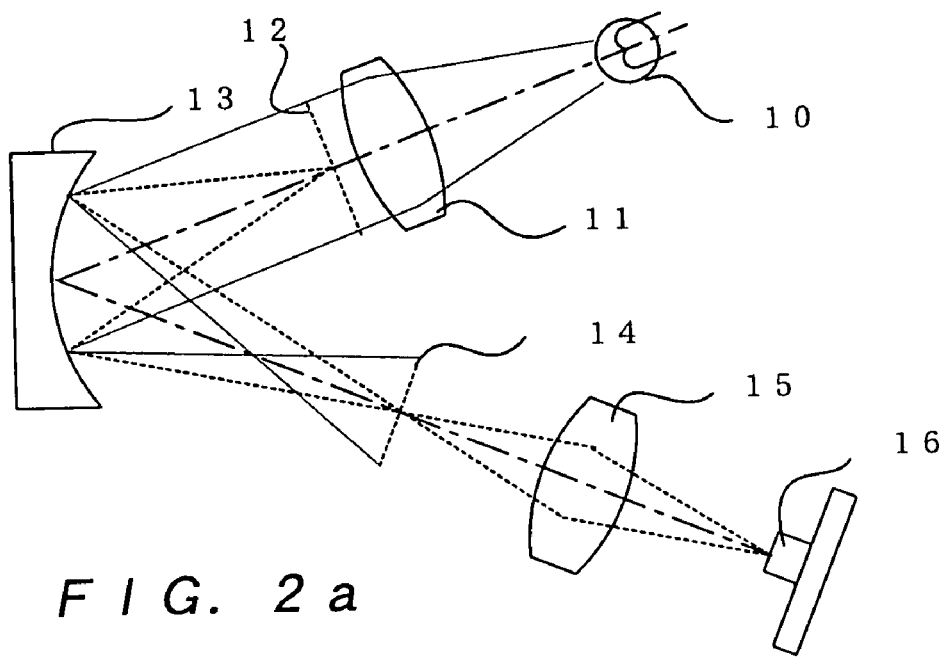
FIG. 2a is an optical diagram of the principle of the measurement of the radius of meniscus curvature.

In FIG. 2a, light from a lamp 10 passes through an objective lens 11 and illuminates a grid 12, used as a light control means, which is projected onto a concave mirror 13 serving as a tear meniscus model. A grid image 14 is formed by the concave mirror 13, and, via a projection lens 15, this grid image 14 is imaged by an imaging means such as a camera 16.

Figure 2B:
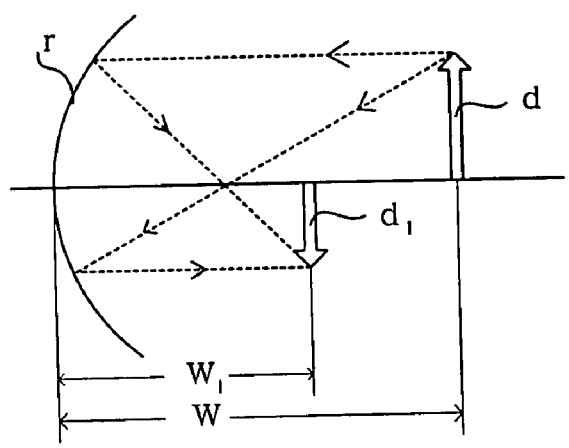
FIG. 2b is a diagram illustrating the formation of a grid image by the tear meniscus.

With respect to FIG. 2b, the grid having a height d at a working distance W from the concave mirror (tear meniscus) of curvature radius r is transformed into an image $d_1$ at a distance $W_1$ from the concave mirror. Here, $W_1=(rW)/(2W-r)$ is obtained from the well-known relationship $2/r=(1/W)+(1/W_1)$, and $d_1=(d/W)\times W_1$ is obtained from the relationship $d_1/d=W_1/W$.

From the above two equations, $$d_1=(d/W)\times\{rW/(2W-r)\},$$

$$d_1=\{dr/(2W-r)\}.$$

Here, if W>>r (for example, W=24, r=0.3), then 2W−r≈2W, providing the approximation formula $d_1\approx(dr/2W)$, thus $r=(d_1/d)\times 2W$.

Figure 2C:
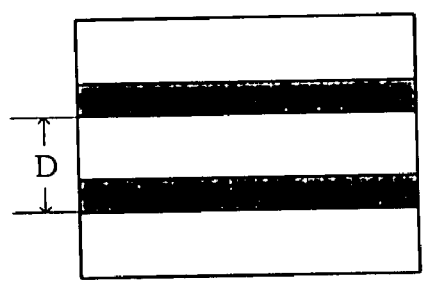
FIG. 2c is a diagram of the grid image displayed on a monitor.

If grid image $d_1$ is magnified by a magnification of β to the size D shown in FIG. 2c, since $D=\beta\times d_1$, then $r=(D/\beta)(2W/d)$. Thus, if the monitor is a 14-inch television monitor, for example, then β=190.9, and as a result, r=(D/190.9)(2W/d).

In grid size (grid pitch), d is a constant, and W is the working distance value determined by the design. While this might be changed somewhat in the alignment, it is a small enough value to be disregarded. Thus, the curvature radius r of the tear meniscus for lacrimal fluid volume V can be found by measuring the size of the grid image D displayed on the monitor.

Figure 3:
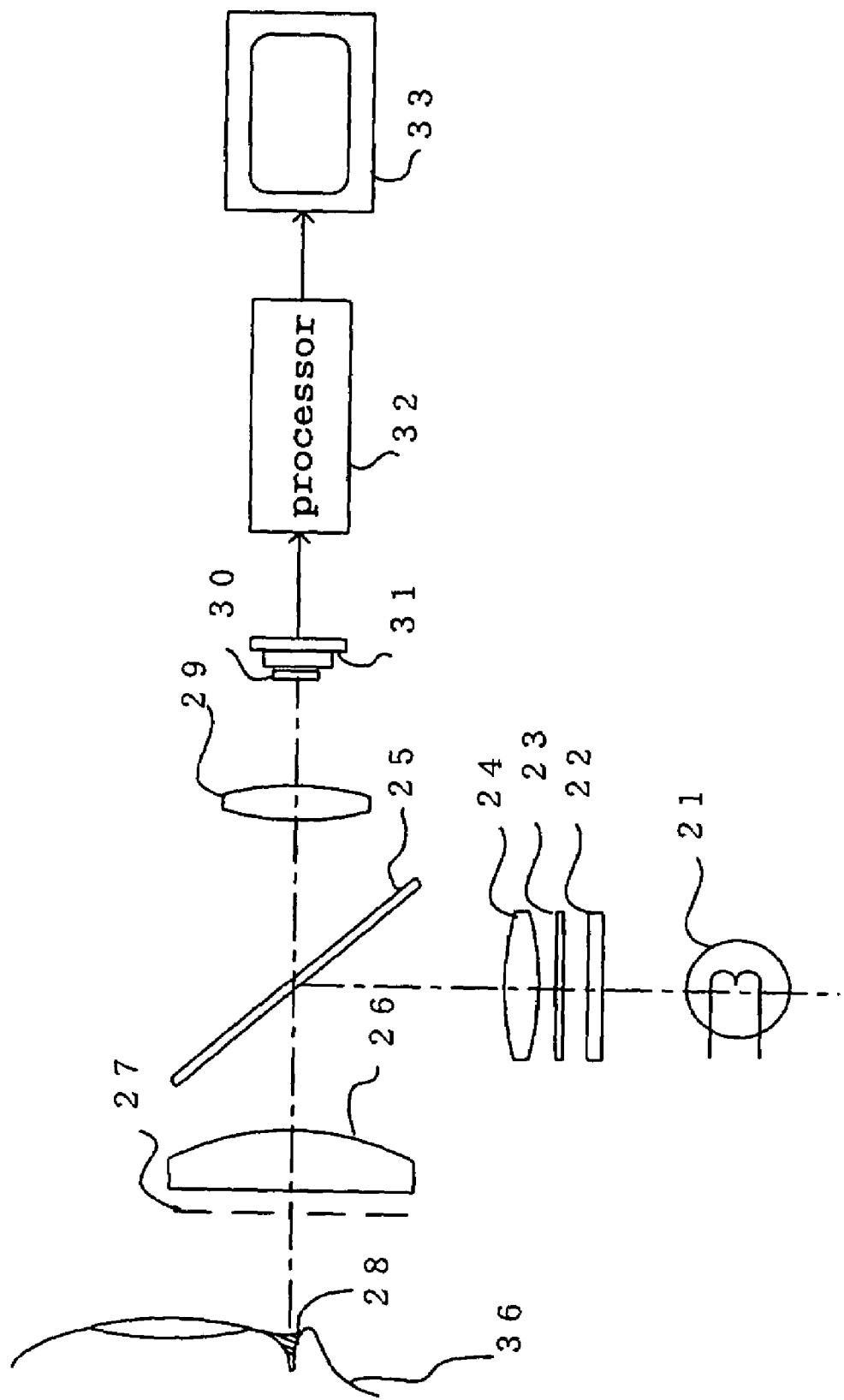
FIG. 3 is a diagram of the arrangement of the apparatus of the invention.

FIG. 3 illustrates a specific apparatus based on the principle described above. With reference to FIG. 3, light from a halogen lamp 21 passes through a filter 22, which blocks heat rays, a polarizing plate 23 and an illumination lens 24, and is reflected by a mirror 25 such as a half-mirror or aperture mirror. The light reflected by the mirror 25 passes through an objective lens 26 and illuminates a grid 27 having a plurality of apertures, that functions as a light control means. The grid 27 thus illuminated is projected onto a meniscus 28 of tear film collected on a lower eyelid 36.

Figure 4:
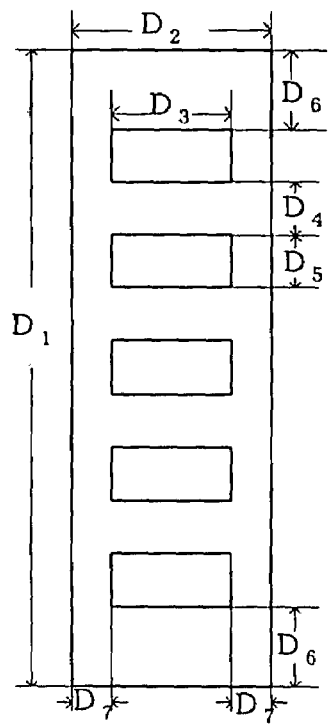
FIG. 4 is a diagram of an example of grid dimensions.

As shown in FIG. 4, the grid 27 comprises a plurality of apertures in the form of slits (five in this example) each measuring $D_3$ by $D_5$ arranged on a $D_1$ by $D_2$ substrate, with the slits being equidistantly spaced apart by a distance $D_4$, and provided with a white space $D_6$ above and below and a white space $D_7$ on each side. The dimensions are set at, for example, the following: $D_1$=48.0 mm, $D_2$=15.0 mm, $D_3$=9.0 mm, $D_4$=4.0 mm, $D_5$=4.0 mm, $D_6$=6.0 mm, and $D_7$=3.0 mm. In this example, the d of FIG. 2b (grid pitch) is $d=D_4+D_5$=8 mm.

The light from the projected grid 27 is reflected by the tear meniscus 28, forming a grid image in the vicinity of the tear meniscus. The grid image thus formed by the tear meniscus passes through objective lens 26, mirror 25, projection lens 29 and polarizing plate 30 and is picked up by a CCD camera 31, and the image is subjected to image processing by a processor 32. This processor 32 can, for example, be used to obtain the pitch of the grid image on the camera corresponding to $d=D_4+D_5$ by binarizing the image signal and obtaining the pixel coordinates for each aperture. The processor 32 also calculates the pitch $d_1$ of the grid image formed by the tear meniscus, taking into account the lens magnification factor, and evaluates the radius of curvature r of the tear meniscus 28 in accordance with the above equation $r=(d_1/d)\times 2W$.

As described above, in the formation of the grid image, the tear meniscus 28 has the function of a concave mirror, and, therefore, the factor by which the grid image formed is magnified depends on the radius of meniscus curvature r of the tear meniscus. Obtaining the radius of meniscus curvature makes it possible to evaluate quantitatively the severity of the dry eye condition. The outcome of each calculation and the evaluation can be displayed on a monitor 33.

The polarizing plate 23 arranged in the illumination and projection system and the polarizing plate 30 arranged in the imaging system both have the same orientation so as to transmit light in the same direction. As the tear meniscus is liquid, the polarized state is not readily broken down in the course of reflection, so using the polarizing plates makes it possible to improve the signal-to-noise (S/N) ratio during imaging.

Figure 5:
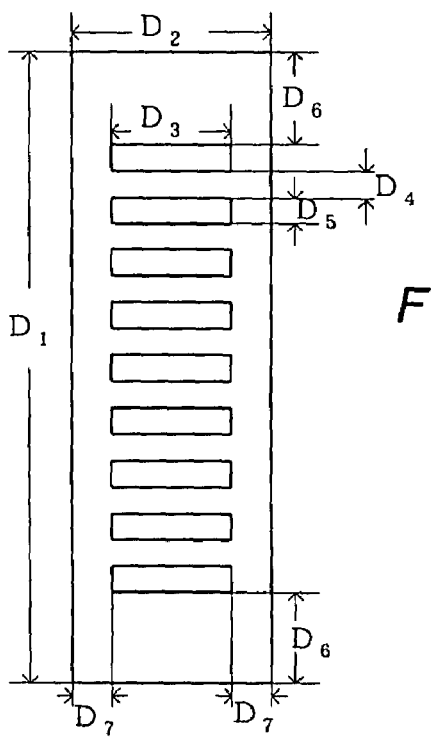
FIG. 5 is a diagram of another example of grid dimensions.

FIG. 5 shows another example of a grid. In this example, the grid has a finer pitch. The dimensions are $D_1$=48.0 mm, $D_2$=15.0 mm, $D_3$=9.0 mm, $D_4$=2.0 mm, $D_5$=2.0 mm, $D_6$=7.0 mm, and $D_7$=3.0 mm, and the grid pitch will be 4 mm.

As to what the degree of precision of r is when the working distance W is 24 mm, the grid pitch is the 8 mm of FIG. 4, and the monitor 33 is a 14-inch model, the following is the result of an actual measurement carried out with the apparatus of FIG. 3 (not using the processor 32), using a glass tube of radius 0.30 mm and piano wire of radius 0.15 mm. In the case of a 14-inch monitor, β=190.9, so from the above equation, curvature radius r will be as follows.

$$r=(D/190.9)\times\{(2\times 24)/8\}=0.0314\times D.$$

In the case of the glass tube of 0.30 mm radius, the grid pitch D on the monitor was 9.55 mm, this being the mean value of ten measurements obtained using a ruler, so r=0.0314×9.55=0.30 mm, an accurate value. In the case of the piano wire of radius 0.15 mm, the average of ten measurements of D was 4.58 mm; so r=0.0314×4.58=0.14 mm. The degree of error is a mere 0.01 mm, confirming that the curvature radius of the meniscus can be measured with quite a degree of precision.

Figure 6:
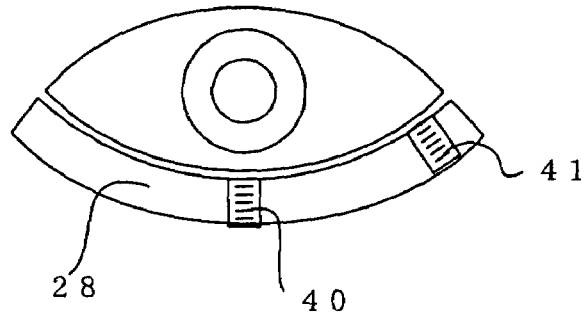
FIG. 6 is a diagram of the grid image projected onto the center and peripheral portions of the tear meniscus.

The tear meniscus 28 is a horizontally elongated shape, with the angle changing going toward the outside corner of the eye. So, by making the grid 27 rotatable, as shown in FIG. 6, the orientation of the grid 27 can be changed between the middle grid image 40 projected on the tear film surface and the peripheral grid image 41. For example, the grid could be adjusted so that straight lines at right-angles to the grid apertures come to a point, making it possible to efficiently direct the illuminating light onto the tear meniscus.

As described in the foregoing, in accordance with the present invention, physical quantities such as the radius of meniscus curvature of tear film can be calculated based on a grid aperture image projected onto the tear film surface, thereby making it possible to quantitatively evaluate the degree of severity or change of a dry eye condition.

What is claimed is:

1. An ophthalmic apparatus comprising:
a grid formed with a plurality of slit-shaped apertures;
means for projecting the apertures onto a surface of a tear film collected on a lower eyelid of a person;
means for imaging the apertures projected on the tear film surface; and
means for evaluating a physical quantity of tear fluid based on the image of the apertures thus obtained,
wherein the grid is disposed on the optical axis so that all the apertures formed on the grid may be projected on the tear film surface.

2. An ophthalmic apparatus according to claim 1; wherein a radius of meniscus curvature is calculated based on the aperture image.

3. An ophthalmic apparatus according to claim 2; wherein a dry eye condition is evaluated based on the calculated radius of meniscus curvature.

4. An ophthalmic apparatus according to claim 1; wherein the apertures are formed on the grid in an equidistant arrangement.

5. An ophthalmic apparatus according to claim 1; wherein the projection means and the imaging means are each provided with a polarizing plate.

6. An ophthalmic apparatus according to claim 1; wherein an optical system of the projection means and an optical system of the imaging means are arranged coaxially.

7. An ophthalmic apparatus comprising:
a grid formed with a plurality of slit-shaped apertures;
means for projecting the apertures onto a surface of a tear film collected on a lower eyelid of a person;
means for imaging the apertures projected on the tear film surface; and
means for evaluating a physical quantity of tear fluid based on the image of the apertures thus obtained,
wherein the apertures are projected so that a straight line at right angles to the aperture image may lie at right angles to a tangent at a point of intersection of the straight line with a curve along the lower eyelid on which the tear film is collected.

8. An ophthalmic apparatus according to claim 7; wherein a radius of meniscus curvature is calculated based on the aperture image.

9. An ophthalmic apparatus according to claim 8; wherein a dry eye condition is evaluated based on the calculated radius of meniscus curvature.

10. An ophthalmic apparatus according to claim 7; wherein the apertures are formed on the grid in an equidistant arrangement.

11. An ophthalmic apparatus according to claim 7; wherein the projection means and imaging means are each provided with a polarizing plate.

12. An ophthalmic apparatus according to claim 7; wherein an optical system of the projection means and an optical system of the imaging means are arranged coaxially.

13. An ophthalmic apparatus comprising:
a grid formed with a plurality of slit-shaped apertures;
means for projecting the apertures onto a surface of a tear film collected on a lower eyelid of a person;
means for imaging the apertures projected on the tear film surface; and
means for evaluating a physical quantity of tear fluid based on the image of the apertures thus obtained,
wherein the grid is changed in orientation between middle and peripheral positions so that a straight line at right angles to the grid aperture image in the middle position may intersect with a straight line at right angles to the grid aperture image in the peripheral position.

14. An ophthalmic apparatus according to claim 13; wherein a radius of meniscus curvature is calculated based on the aperture image.

15. An ophthalmic apparatus according to claim 14; wherein a dry eye condition is evaluated based on the calculated radius of meniscus curvature.

16. An ophthalmic apparatus according to claim 13; wherein the apertures are formed on the grid in an equidistant arrangement.

17. An ophthalmic apparatus according to claim 13; wherein the projection means and imaging means are each provided with a polarizing plate.

18. An ophthalmic apparatus according to claim 13; wherein an optical system of the projection means and an optical system of the imaging means are arranged coaxially.

* * * * *